(12) United States Patent
Yamada et al.

(10) Patent No.: US 12,316,944 B2
(45) Date of Patent: May 27, 2025

(54) IMAGE PICKUP DEVICE AND ENDOSCOPE

(71) Applicant: FUJIFILM Corporation, Tokyo (JP)

(72) Inventors: Hideyuki Yamada, Kanagawa (JP); Takuro Asaoka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 52 days.

(21) Appl. No.: 18/069,154

(22) Filed: Dec. 20, 2022

(65) Prior Publication Data

US 2023/0131639 A1 Apr. 27, 2023

Related U.S. Application Data

(63) Continuation of application No. PCT/JP2021/027444, filed on Jul. 26, 2021.

(30) Foreign Application Priority Data

Jul. 30, 2020 (JP) ................................. 2020-129459

(51) Int. Cl.
*H04N 23/50* (2023.01)
*A61B 1/00* (2006.01)
(Continued)

(52) U.S. Cl.
CPC ....... *H04N 23/555* (2023.01); *A61B 1/00096* (2013.01); *A61B 1/051* (2013.01);
(Continued)

(58) Field of Classification Search
CPC ...... H04N 23/555; H04N 23/51; H04N 23/55; H04N 23/56; A61B 1/00096; A61B 1/051;
(Continued)

(56) References Cited

U.S. PATENT DOCUMENTS 6,773,392 B2 * 8/2004 Kikuchi ................. A61B 1/051
600/129
7,713,189 B2 5/2010 Hanke
(Continued)

FOREIGN PATENT DOCUMENTS

JP 2017-500997 A 1/2017

OTHER PUBLICATIONS

International Search Report issued in PCT/JP2021/027444; mailed Sep. 7, 2021.
(Continued)

*Primary Examiner* — Michael Lee
(74) *Attorney, Agent, or Firm* — Studebaker Brackett PLLC

(57) ABSTRACT

An image pickup device that is provided at a distal end portion of an insertion unit of an endoscope having a longitudinal axis, includes: a first lens barrel that houses a first optical system; a second lens barrel that is disposed on a proximal end side of the first lens barrel, houses a second optical system on which light having passed through the first optical system is to be incident, and includes a second lens barrel-distal end portion that is a distal end portion having a diameter smaller than a diameter of a first lens barrel-proximal end portion which is a proximal end portion of the first lens barrel; a sliding part that is provided around an outer peripheral surface of the second lens barrel-distal end portion and that is in contact with the first lens barrel-proximal end portion; and a pressing member that is externally fitted over the sliding part from the first lens barrel-proximal end portion. The pressing member includes a pressing member-inner peripheral surface that is in contact with both an outer peripheral surface of the first lens barrel-proximal end portion and an outer peripheral surface of the sliding part, and a movement restricting portion that
(Continued)

restricts a movement of the sliding part in an axial direction of the longitudinal axis between the first lens barrel-proximal end portion and the movement restricting portion.

20 Claims, 13 Drawing Sheets

(51) Int. Cl.
    *A61B 1/05*     (2006.01)
    *G02B 7/02*     (2021.01)
    *H04N 23/51*     (2023.01)
    *H04N 23/55*     (2023.01)

(52) U.S. Cl.
    CPC ............. *G02B 7/021* (2013.01); *H04N 23/51* (2023.01); *H04N 23/55* (2023.01)

(58) Field of Classification Search
    CPC ..... A61B 1/0011; A61B 1/00179; A61B 1/04; G02B 7/021; G02B 23/243; G02B 23/24
    See application file for complete search history.

(56) References Cited

U.S. PATENT DOCUMENTS

| | | | |
|---|---|---|---|
| 11,693,226 B2 * | 7/2023 | Yamada | A61B 1/05 600/112 |
| 2005/0238347 A1 * | 10/2005 | Oh | G03B 9/06 396/449 |
| 2006/0058581 A1 | 3/2006 | Hanke | |
| 2010/0245653 A1 * | 9/2010 | Bodor | G02B 23/243 348/335 |
| 2012/0220828 A1 * | 8/2012 | Iwasaki | A61B 1/0051 600/109 |
| 2015/0164312 A1 | 6/2015 | Hoyle et al. | |
| 2017/0082848 A1 * | 3/2017 | Kudo | A61B 1/00163 |
| 2018/0035877 A1 * | 2/2018 | Kinouchi | A61B 1/0676 |
| 2018/0039062 A1 * | 2/2018 | Yamada | G02B 23/24 |

OTHER PUBLICATIONS

International Preliminary Report On Patentability (Chapter I) and Written Opinion of the International Searching Authority issued in PCT/JP2021/027444; issued Jan. 31, 2023.

\* cited by examiner

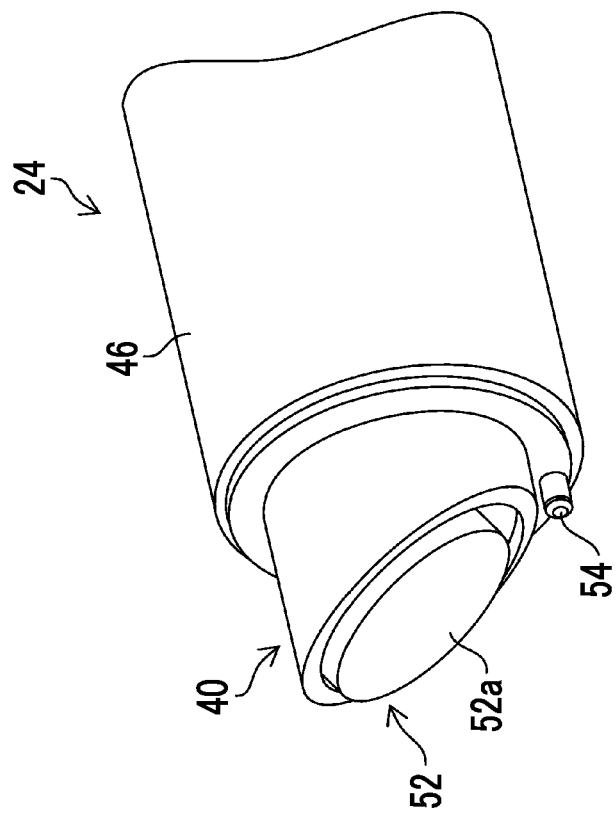
FIG. 6
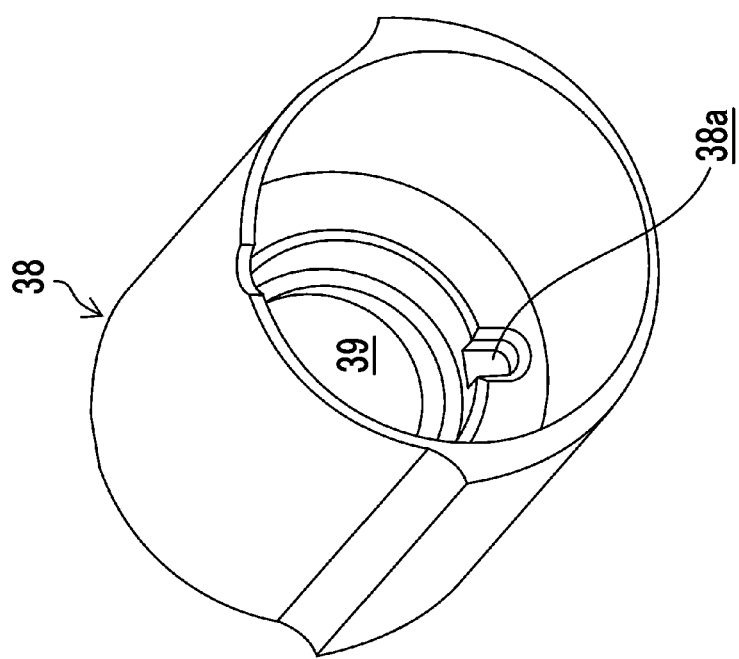

IMAGE PICKUP DEVICE AND ENDOSCOPE

CROSS-REFERENCE TO RELATED APPLICATIONS

The present application is a Continuation of PCT International Application No. PCT/JP2021/027444 filed on Jul. 26, 2021 claiming priority under 35 U.S.C § 119(a) to Japanese Patent Application No. 2020-129459 filed on Jul. 30, 2020. Each of the above applications is hereby expressly incorporated by reference, in its entirety, into the present application.

BACKGROUND OF THE INVENTION

1. Field of the Invention

The present invention relates to an image pickup device that is provided at a distal end portion of an insertion unit of an endoscope and an endoscope comprising the image pickup device.

2. Description of the Related Art

A rigid endoscope is known as an endoscope used for endoscopic surgery or the like. Further, an oblique-viewing endoscope of which a diagonal front side with respect to a longitudinal axis of an insertion unit corresponds to a visual field direction is known as this rigid endoscope. For example, the oblique-viewing endoscope comprises a protection sheath in which a cover glass is fixed to a distal end thereof, an inner sheath that is inserted into the protection sheath, and an image pickup device that is provided at a distal end portion of the inner sheath.

For example, the image pickup device comprises a first lens barrel, a second lens barrel, a rotary pipe, a first bearing member, a second bearing member, and an image pickup element (see U.S. Pat. No. 7,713,189B). The first lens barrel is fixed to a distal end portion in the inner sheath, and houses an oblique-viewing optical system (first optical system). The second lens barrel is disposed on a proximal end side of the first lens barrel in the inner sheath, and houses an optical system (second optical system). The rotary pipe is connected to a proximal end portion of the second lens barrel. The first bearing member is provided between an inner peripheral surface of the inner sheath and an outer peripheral surface of the second lens barrel. The second bearing member is provided between the inner peripheral surface of the inner sheath and an outer peripheral surface of the rotary pipe. The image pickup element is disposed at a proximal end portion in the second lens barrel, and picks up an image of light that is incident through each of the optical systems of the first lens barrel and the second lens barrel.

The first lens barrel and the second lens barrel of the image pickup device disclosed in U.S. Pat. No. 7,713,189B are rotatable relative to each other in circumferential directions of the first lens barrel and the second lens barrel via the first bearing member. Further, a clearance is formed between the outer peripheral surface of the second lens barrel and the first bearing member in the image pickup device disclosed in U.S. Pat. No. 7,713,189B.

SUMMARY OF THE INVENTION

In a case where errors, such as a surface tilt (the tilt of an optical axis), the deflection of an optical axis (the eccentricity of an optical axis), and backlash, occur in the image pickup device having a three-piece structure, which includes the first lens barrel, the second lens barrel, and the bearing member (first bearing member) disclosed in U.S. Pat. No. 7,713,189B, optical performance is adversely affected. Accordingly, in the image pickup device, it is necessary to precisely control the component accuracy (machining accuracy) of each component to make a fitting dimensional tolerance extremely small, and highly accurate optical adjustment is required. For this reason, steps of positioning, assembling, and adjusting the respective components are complicated. Further, since the number of components is increased and the component accuracy for each component is required, cost is increased. Furthermore, since the image quality inspection of the image pickup device can be performed for the first time after the assembly and adjustment of each component, there is a concern that the number of defective products will be increased.

Moreover, since a clearance is formed between the outer peripheral surface of the second lens barrel and the first bearing member in the image pickup device disclosed in U.S. Pat. No. 7,713,189B, a surface tilt, the deflection of an optical axis, and backlash are likely to occur, and optical performance is adversely affected.

The present invention has been made in consideration of such circumstances, and an object of the present invention is to provide an image pickup device from which good optical performance is obtained and an endoscope comprising the image pickup device.

In order to achieve the object of the present invention, according to an aspect of the present invention, there is provided an image pickup device that is provided at a distal end portion of an insertion unit of an endoscope having a longitudinal axis. The image pickup device comprises: a first lens barrel that houses a first optical system; a second lens barrel that is disposed on a proximal end side of the first lens barrel, houses a second optical system on which light having passed through the first optical system is to be incident, and includes a second lens barrel-distal end portion that is a distal end portion having a diameter smaller than a diameter of a first lens barrel-proximal end portion which is a proximal end portion of the first lens barrel; a sliding part that is provided around an outer peripheral surface of the second lens barrel-distal end portion and that is in contact with the first lens barrel-proximal end portion; and a pressing member that is externally fitted over the sliding part from the first lens barrel-proximal end portion. The pressing member includes a pressing member-inner peripheral surface that is in contact with both an outer peripheral surface of the first lens barrel-proximal end portion and an outer peripheral surface of the sliding part, and a movement restricting portion that restricts a movement of the sliding part in an axial direction of the longitudinal axis between the first lens barrel-proximal end portion and the movement restricting portion, and the first lens barrel and the second lens barrel are rotatable relative to each other in circumferential directions of the first lens barrel and the second lens barrel via the sliding part and the pressing member.

According to this image pickup device, the occurrence of a surface tilt, the deflection of optical axes, and backlash of the first optical system and the second optical system are prevented without requiring complicated optical adjustment during assembly, so that good optical performance is obtained.

According to another aspect of the present invention, the image pickup device further comprises an image pickup unit that picks up an image of light incident through the first optical system and the second optical system.

According to another aspect of the present invention, in the image pickup device, the image pickup unit includes a refractive optical element that refracts light incident from the second optical system, and an image pickup element that picks up an image of the light refracted by the refractive optical element.

According to another aspect of the present invention, in the image pickup device, the image pickup unit includes an image pickup element that is disposed on a proximal end side of the second optical system and that includes a light-receiving surface orthogonal to an optical axis of the second optical system.

According to another aspect of the present invention, the image pickup device further comprises a tubular holder that is connected and fixed to the second lens barrel from a proximal end side of the second lens barrel and that holds the image pickup unit.

According to another aspect of the present invention, in the image pickup device, the second lens barrel and the sliding part are formed separately from each other, and the sliding part is externally fitted and fixed to the outer peripheral surface of the second lens barrel-distal end portion. Accordingly, the sliding part can be made of a material different from the material of the second lens barrel, for example, a material having good sliding between itself and the first lens barrel and the pressing member.

According to another aspect of the present invention, the image pickup device further comprises a first protruding portion that is provided around a distal end side of the outer peripheral surface of the second lens barrel-distal end portion; and a fitting hole which is formed in a first lens barrel-proximal end surface that is a proximal end surface of the first lens barrel-proximal end portion and to which the first protruding portion is fitted, and the sliding part is externally fitted and fixed to the outer peripheral surface of the second lens barrel-distal end portion in a state where the sliding part is in contact with the first protruding portion from a proximal end side of the first protruding portion. Accordingly, the sliding part can be abutted against the first lens barrel-proximal end surface of the first lens barrel using the first protruding portion and the fitting hole as guides.

According to another aspect of the present invention, the image pickup device further comprises an integrally molded body in which the second lens barrel-distal end portion of the second lens barrel and the sliding part are integrated with each other. Accordingly, the assembly man-hours for the image pickup device can be reduced.

According to another aspect of the present invention, in the image pickup device, a material of the sliding part is different from a material of the first lens barrel and a material of the pressing member. Accordingly, close contact (so-called galling) between the sliding part and the first lens barrel and close contact between the sliding part and the pressing member can be prevented.

According to another aspect of the present invention, in the image pickup device, the pressing member-inner peripheral surface includes a fixed region that is fixed to the outer peripheral surface of the first lens barrel-proximal end portion, and a sliding region with which the outer peripheral surface of the sliding part is in sliding contact. Accordingly, the first lens barrel and the second lens barrel can be rotated relative to each other in the circumferential directions thereof.

According to another aspect of the present invention, the image pickup device further comprises an antireflection layer that is formed on an inner peripheral surface of the first lens barrel and on an inner peripheral surface of the second lens barrel, and a surface of the first lens barrel that is in contact with the sliding part and surfaces of the sliding part that are in contact with the first lens barrel and the pressing member are surfaces on which the antireflection layer is not formed. Accordingly, the reflection of light in the first lens barrel and the second lens barrel can be suppressed, and the high dimensional accuracy of a sliding surface between the first lens barrel and the sliding part and a sliding surface between the sliding part and the pressing member can be ensured.

According to another aspect of the present invention, in the image pickup device, the first lens barrel-proximal end portion is a diameter-increased portion of which a diameter is larger than diameters of other portions of the first lens barrel.

According to another aspect of the present invention, in the image pickup device, an outer diameter of the first lens barrel-proximal end portion and an outer diameter of the sliding part are equal to each other.

According to another aspect of the present invention, in the image pickup device, a first lens barrel-proximal end surface that is a proximal end surface of the first lens barrel-proximal end portion and a sliding part-distal end surface that is a distal end surface of the sliding part are surfaces perpendicular to the longitudinal axis, the sliding part-distal end surface is in contact with the first lens barrel-proximal end surface, and the movement restricting portion restricts the movement of the sliding part in the axial direction between the first lens barrel-proximal end surface and the movement restricting portion. Accordingly, the movement of the sliding part in the axial direction can be restricted in a state where the sliding part-distal end surface is abutted against the first lens barrel-proximal end surface.

According to another aspect of the present invention, in the image pickup device, a proximal end portion of the pressing member extends to a proximal end side beyond a proximal end portion of the sliding part, the movement restricting portion is a second protruding portion that is provided around the pressing member-inner peripheral surface at the proximal end portion of the pressing member, the second protruding portion is in contact with a sliding part-proximal end surface, which is a proximal end surface of the sliding part, to restrict the movement of the sliding part in the axial direction between the first lens barrel-proximal end surface and the second protruding portion, and the sliding part-proximal end surface and a contact surface of the second protruding portion, which is in contact with the sliding part-proximal end surface, are surfaces perpendicular to the longitudinal axis. Accordingly, the movement of the sliding part in the axial direction can be restricted.

According to another aspect of the present invention, in the image pickup device, the first optical system is an oblique-viewing optical system that guides light, which is incident in a direction inclined with respect to the longitudinal axis, to the second optical system.

According to another aspect of the present invention, in the image pickup device, the oblique-viewing optical system includes a light incident surface that is inclined from a posture perpendicular to the longitudinal axis, and includes a tubular cover that is provided at a distal end portion of the first lens barrel and that covers the distal end portion of the first lens barrel, a cover glass that is provided at a distal end portion in the cover and that has an inclined posture corresponding to an inclination angle of the light incident surface, and a positioning portion that is provided on the first lens barrel and that is engaged with an engaged portion provided in the cover to set a rotational position of the first lens barrel in the cover in the circumferential direction to a position where the light incident surface faces the cover glass. Accordingly, the mounting of the cover on the first lens barrel can be easily performed.

According to another aspect of the present invention, the image pickup device further comprises an image pickup unit that picks up an image of light incident through the first optical system and the second optical system and a cable that is connected to the image pickup unit, and a cable proximal end portion opposite to a cable distal end portion of the cable to be connected to the image pickup unit is adapted to be torsionally deformable. Accordingly, in a case where the second lens barrel is rotated relative to the first lens barrel in the circumferential direction thereof, the disconnection of the cable can be prevented.

In order to achieve the object of the present invention, according to another aspect of the present invention, there is provided an endoscope comprising: an insertion unit that has a longitudinal axis; and the above-mentioned image pickup device that is provided at a distal end portion of the insertion unit.

According to another aspect of the present invention, in the endoscope, the image pickup device includes an image pickup unit that picks up an image of light incident through the first optical system and the second optical system, and a tubular holder that is connected and fixed to the second lens barrel from a proximal end side of the second lens barrel and that holds the image pickup unit, and the endoscope includes a tubular torque tube that is rotatable in the circumferential direction, and a tubular connecting pipe that connects the holder to the torque tube and that transmits rotary torque of the torque tube to the holder. Since the torque tube is used, the transmission of torque other than rotary torque to the connecting pipe and the like is suppressed. Accordingly, the durability of the connecting pipe and the like can be improved.

According to the present invention, good optical performance is obtained.

BRIEF DESCRIPTION OF THE DRAWINGS

FIG. 6 is a diagram illustrating the mounting of a cover on the first lens barrel.

DESCRIPTION OF THE PREFERRED EMBODIMENTS

First Embodiment

Figure 1:
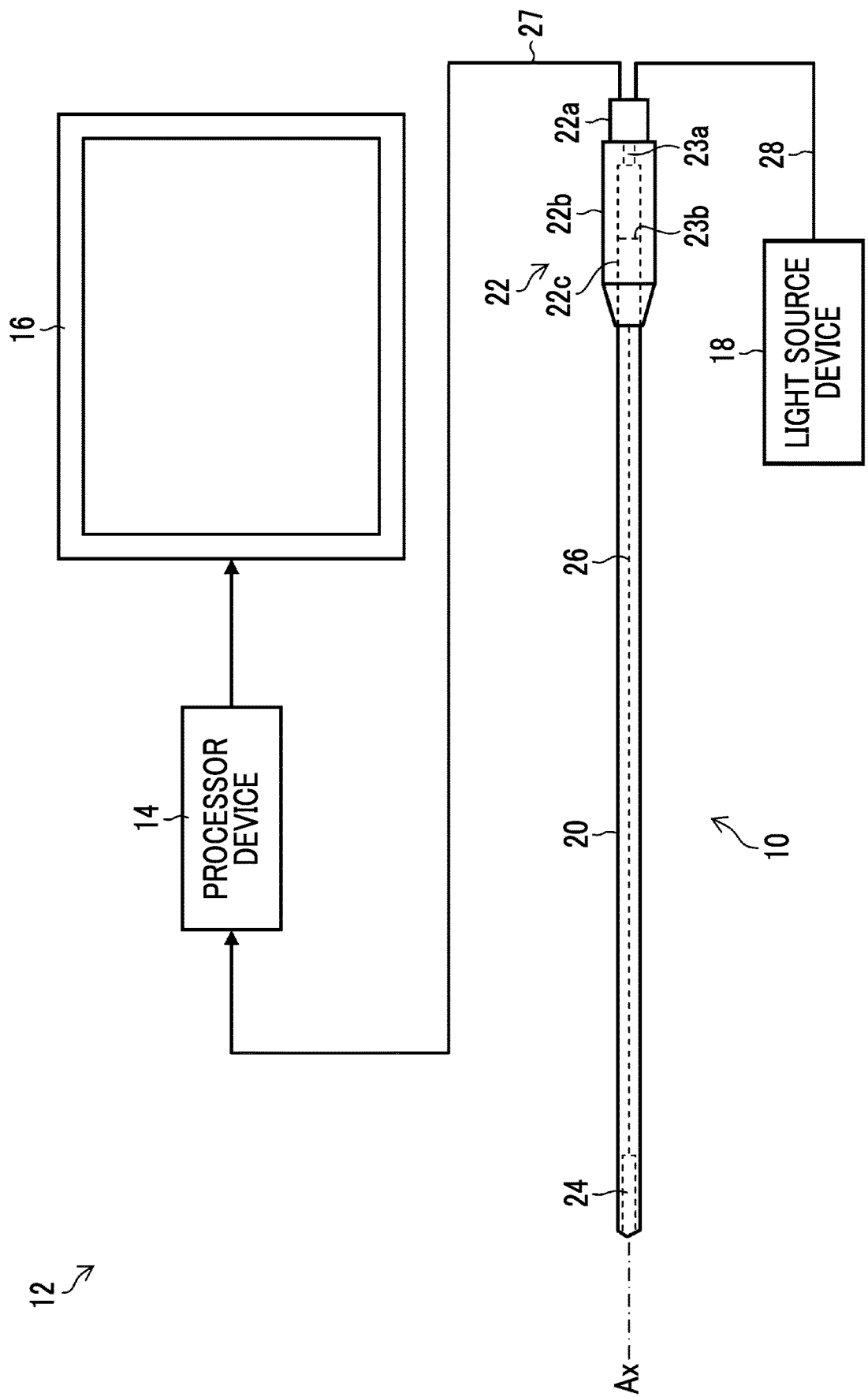
FIG. 1 is a diagram showing the configuration of an endoscope system that comprises an oblique-viewing endoscope according to a first embodiment.

FIG. 1 is a diagram showing the configuration of an endoscope system 12 that comprises an oblique-viewing endoscope 10 according to a first embodiment. As shown in FIG. 1, the endoscope system 12 comprises an oblique-viewing endoscope 10 corresponding to an endoscope of the present invention, a processor device 14, a monitor 16, and a light source device 18.

The oblique-viewing endoscope 10 is a so-called rigid endoscope, and comprises an insertion unit 20, an operation unit 22, and an image pickup device 24. The insertion unit 20 is formed in a substantially tubular shape, and is to be inserted into a patient's body. The insertion unit 20 has a distal end, a proximal end, and a longitudinal axis Ax. The image pickup device 24 (also referred to as a camera unit) to be described later is provided at a distal end portion of the insertion unit 20. Further, a signal cable 26 (corresponding to a cable of the present invention) and a light guide 28 (optical fiber cable) are inserted into the insertion unit 20. In order to not complicate the drawings, the light guide 28 inserted into the insertion unit 20 is not shown.

The signal cable 26 is connected to the image pickup device 24 and to the processor device 14 to be described later together with a signal cable 27 to be described later. A distal end portion of the signal cable 26 is connected to the image pickup device 24, and a proximal end portion of the signal cable 26 is connected to an air-tight connector (not shown) provided on a partition wall 23b to be described later. A distal end portion (light emitting end surface) of the light guide 28 is provided on a distal end surface of the insertion unit 20, and a proximal end portion (light incident end surface) thereof is connected to the light source device 18.

The operation unit 22 is connected to a proximal end portion of the insertion unit 20. The operation unit 22 comprises a base 22a, a rotary part 22b, and an air-tight case 22c.

The base 22a is formed substantially in the shape of a tube parallel to the longitudinal axis Ax. The rotary part 22b is held at a distal end portion of the base 22a to be rotatable relative to the base 22a in a circumferential direction thereof. "The circumferential direction of" described in this specification indicates a direction around the longitudinal axis Ax or an axis parallel to the longitudinal axis Ax.

The rotary part 22b is formed substantially in the shape of a tube parallel to the longitudinal axis Ax. A sheath pipe 30 (see FIG. 2) to be described later is connected to a distal end portion of the rotary part 22b. In a case where the rotary part 22b is rotated relative to the base 22a in the circumferential direction thereof, a visual field direction (observation direction, see an optical axis OA shown in FIG. 2) of the oblique-viewing endoscope 10 can be rotated in the same direction as the circumferential direction.

The air-tight case 22c is provided in the rotary part 22b. The air-tight case 22c is formed substantially in the shape of a tube parallel to the longitudinal axis Ax, and forms an air-tight space together with a cover glass 39, a protection sheath 32, and the like shown in FIG. 2 to be described later. The protection sheath 32 is connected to a distal end portion of the air-tight case 22c. Further, in the air-tight case 22c, a cable holding part 23a is held to be rotatable in the circumferential direction, and the partition wall 23b is provided.

The cable holding part 23a has a shape extending along the longitudinal axis Ax, and holds the signal cable 26. Further, a torque tube 64 (see FIG. 7) to be described later is connected to a distal end portion of the cable holding part 23a, and the base 22a is connected to a proximal end portion of the cable holding part 23a. Accordingly, the rotary part 22b and the air-tight case 22c are rotatable independently of the cable holding part 23a, the signal cable 26, and the base 22a, so that the rotation of one side thereof is not transmitted to the other thereof.

The partition wall 23b hermetically seals a proximal end-side opening of the above-mentioned air-tight space that is formed by the air-tight case 22c and the like. An air-tight connector (not shown) is provided on this partition wall 23b. A proximal end portion of the signal cable 26 and a distal end portion of the already described signal cable 27 are connected to each other via this air-tight connector. A proximal end portion of the signal cable 27 is connected to the processor device 14. Accordingly, the image pickup device 24 and the processor device 14 are connected to each other via the signal cables 26 and 27.

The processor device 14 generates a captured image (video image) of the inside of the patient's body on the basis of image pickup signals input from the image pickup device 24 via the signal cables 26 and 27, and causes the monitor 16 to display this captured image.

The light source device 18 supplies illumination light to the light guide 28. Accordingly, illumination light is emitted from the light emitting end surface of the distal end portion of the light guide 28 that is provided on the distal end surface of the insertion unit 20.

Figure 2:
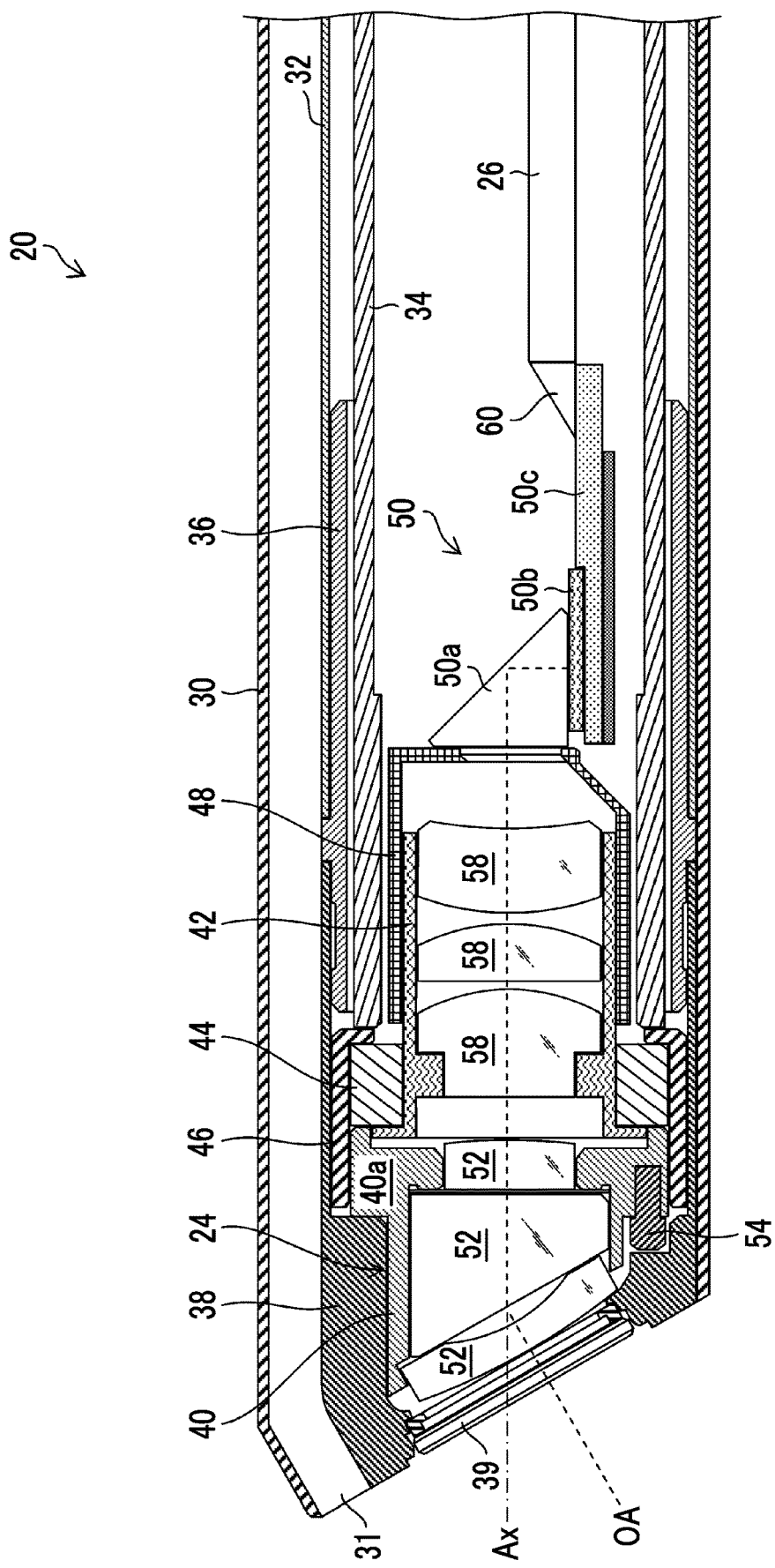
FIG. 2 is an enlarged cross-sectional view of a distal end portion of an insertion unit.

FIG. 2 is an enlarged cross-sectional view of the distal end portion of the insertion unit 20. As shown in FIG. 2, the insertion unit 20 comprises a sheath pipe 30 that is formed substantially in the shape of a tube parallel to the longitudinal axis Ax, a protection sheath 32, and a connecting pipe 34 (also referred to as an inner sheath). The sheath pipe 30 forms an outer peripheral wall of the insertion unit 20. An opening of a distal end portion of the sheath pipe 30 is inclined from a posture perpendicular to the longitudinal axis Ax. Further, a proximal end portion of the sheath pipe 30 is connected to the rotary part 22b as already described. Accordingly, the sheath pipe 30 is rotated integrally with the rotary part 22b.

The protection sheath 32 is inserted into and disposed in the sheath pipe 30. A proximal end portion of a cover holding part 36, which is formed substantially in the shape of a tube parallel to the longitudinal axis Ax, is fitted and fixed to a distal end-side opening portion of the protection sheath 32. Further, the air-tight case 22c is connected to a proximal end portion of the protection sheath 32 as already described.

The connecting pipe 34 is inserted into and disposed in the protection sheath 32. A distal end portion of the connecting pipe 34 protrudes toward a distal end side of the insertion unit 20 beyond a distal end portion of the cover holding part 36. Further, the torque tube 64 (see FIG. 7) to be described later is connected to a proximal end portion of the connecting pipe 34. Furthermore, the image pickup device 24 to be described later is mounted on the distal end portion of the connecting pipe 34. Reference character OA shown in FIG. 2 denotes the optical axis of the optical system of the image pickup device 24.

A cover 38 (also referred to as a case or a cap) covering the image pickup device 24 is mounted on the distal end portion of the cover holding part 36. The cover 38 forms the distal end portion of the insertion unit 20, and is formed substantially in the shape of a tube parallel to the longitudinal axis Ax. The cover glass 39, which has an inclined posture corresponding to an inclination angle of a light incident surface 52a (see FIG. 3) of an oblique-viewing optical system 52 to be described later, is provided at a distal end-side opening portion of the cover 38.

An insertion passage 31 for the light guide 28 (not shown in FIG. 2) is formed between an inner peripheral surface of the sheath pipe 30 and an outer peripheral surface of the protection sheath 32.

[Image Pickup Device According to First Embodiment]

Figure 3:
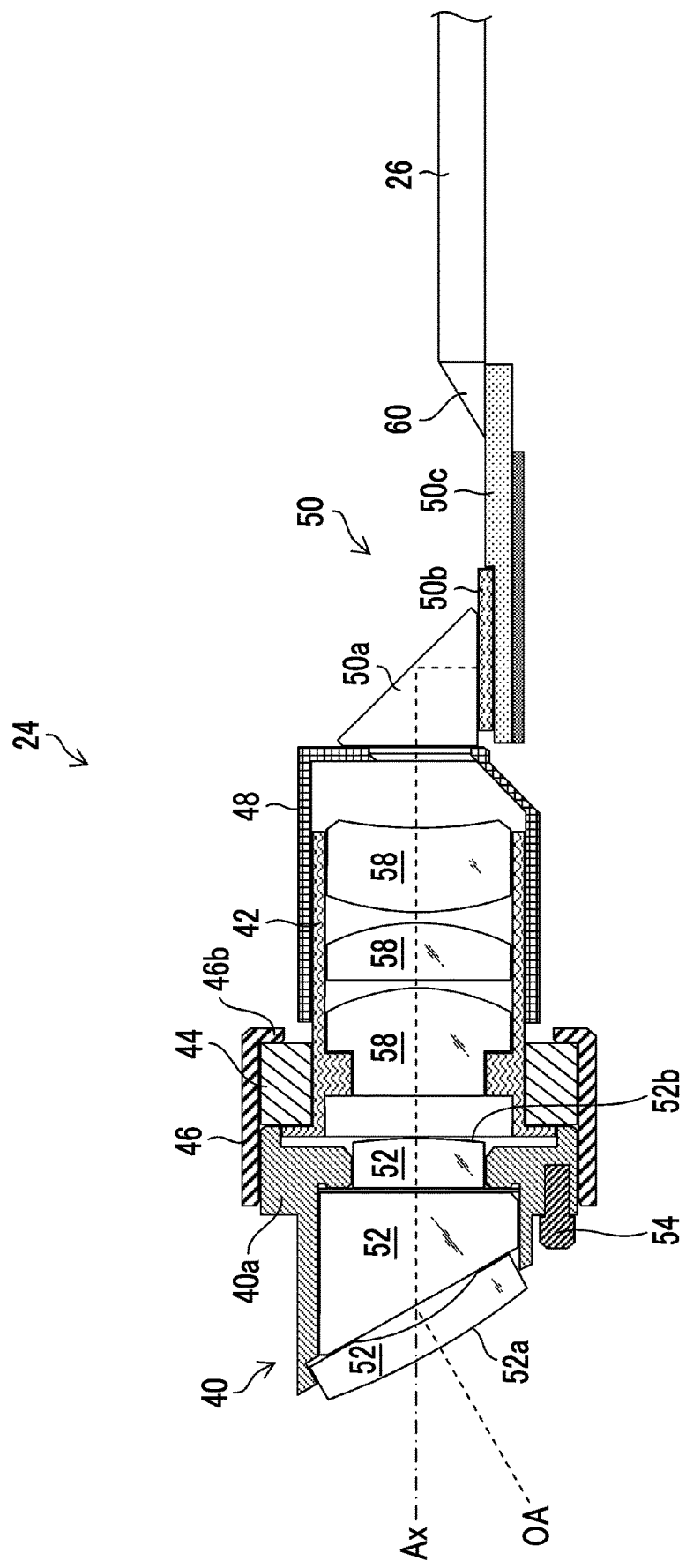
FIG. 3 is a cross-sectional view of an image pickup device.
Figure 4:
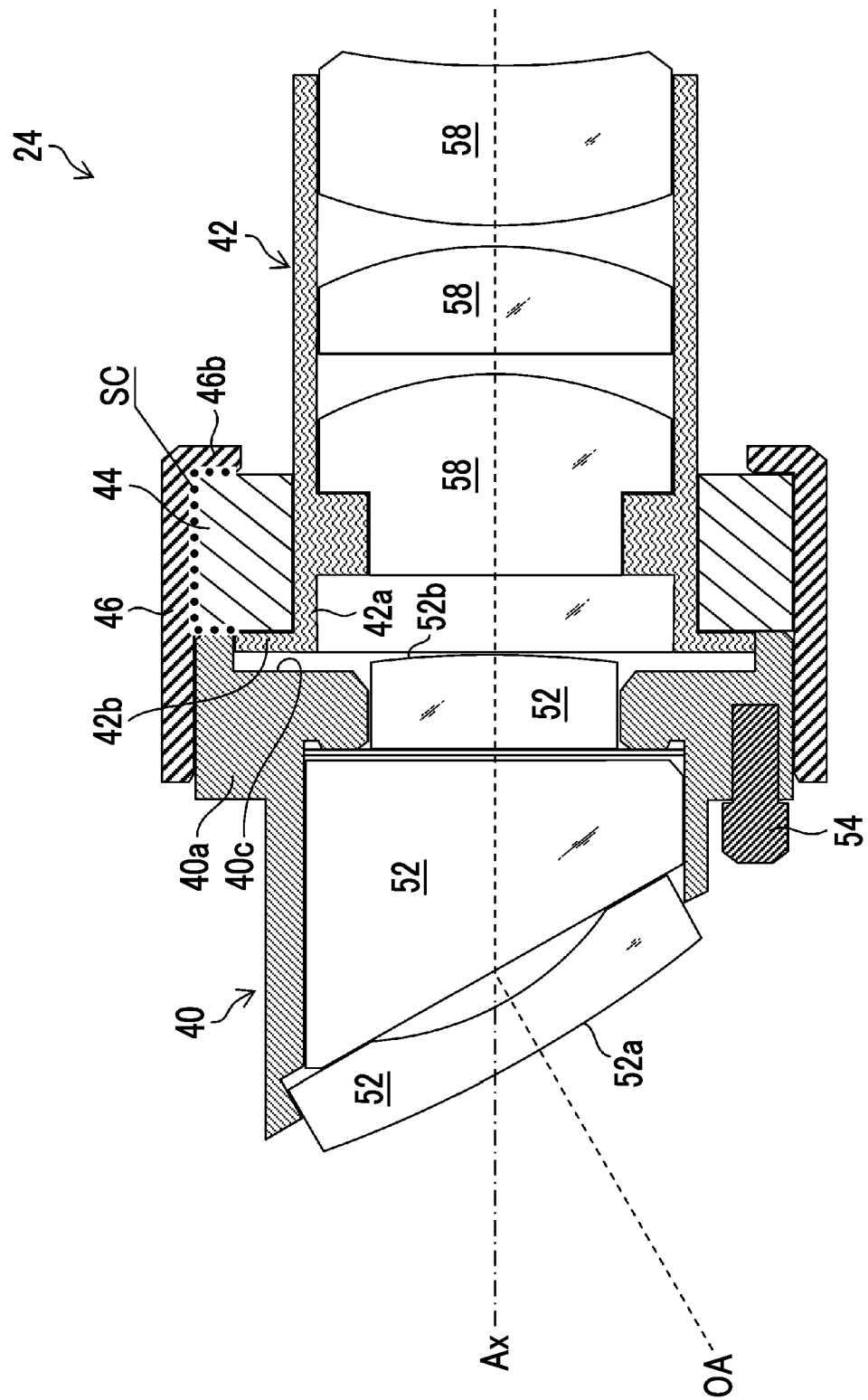
FIG. 4 is an enlarged view of a first lens barrel, a second lens barrel, a sliding part, and a pressing member of the image pickup device shown in FIG. 3.
Figure 5:
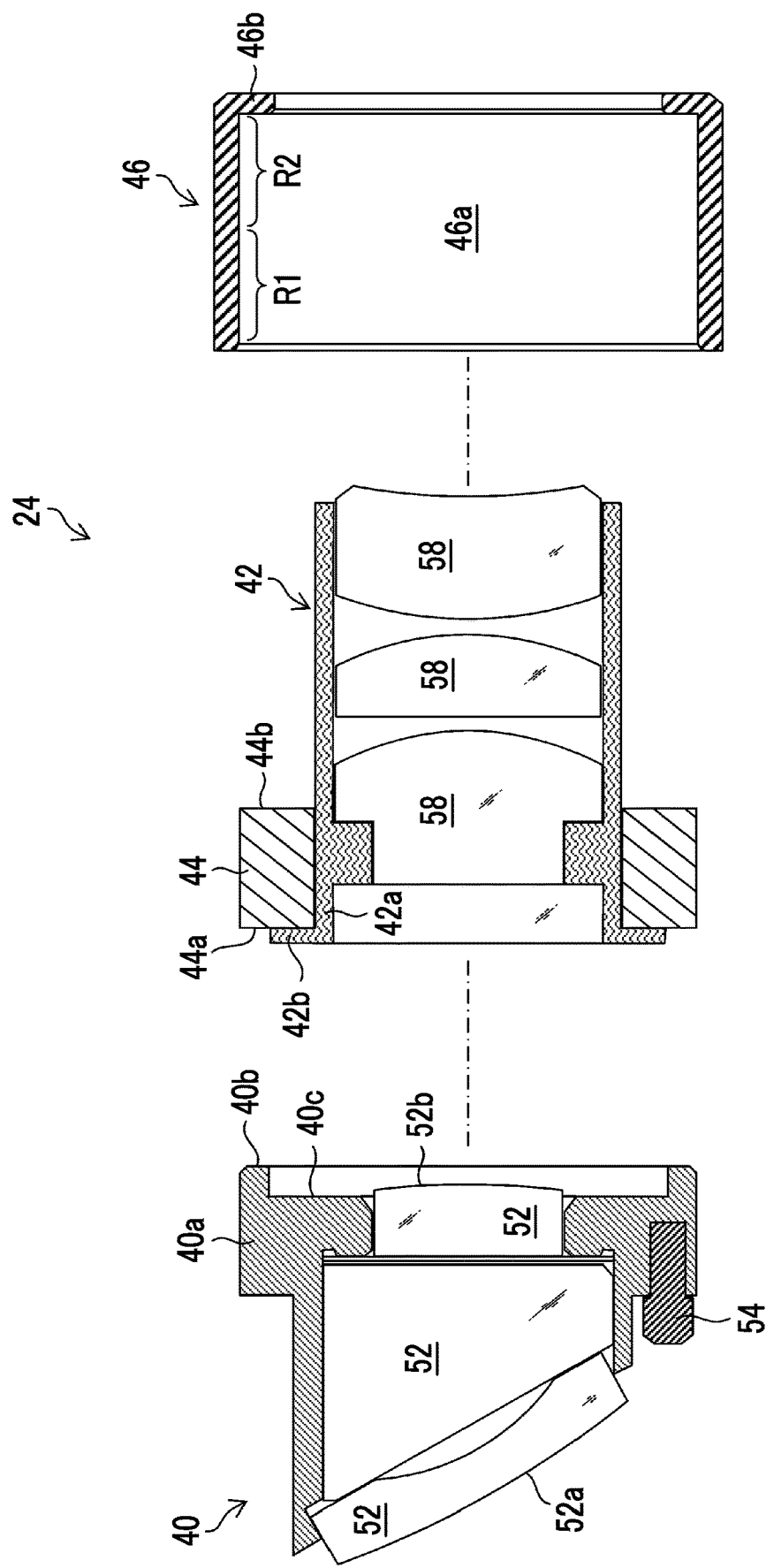
FIG. 5 is an exploded view of the image pickup device shown in FIG. 4.

FIG. 3 is a cross-sectional view of the image pickup device 24. FIG. 4 is an enlarged view of a first lens barrel 40, a second lens barrel 42, a sliding part 44, and a pressing member 46 of the image pickup device 24 shown in FIG. 3. FIG. 5 is an exploded view of the image pickup device 24 shown in FIG. 4. As shown in FIGS. 3 to 5 and in already described FIG. 2, the image pickup device 24 captures an image in a direction inclined with respect to the longitudinal axis Ax, that is, diagonally in front of the distal end portion of the insertion unit 20.

The image pickup device 24 comprises a first lens barrel 40, a second lens barrel 42, a sliding part 44 (also referred to as a bearing), a pressing member 46, a holder 48, an image pickup unit 50, and the already described signal cable 26.

For example, the first lens barrel 40 is made of a metal material, such as stainless steel, and is formed substantially in the shape of a tube parallel to the longitudinal axis Ax. The oblique-viewing optical system 52 is housed in the first lens barrel 40. Further, a diameter-increased portion 40a of which a diameter is larger than the diameters of other portions of the first lens barrel 40 is formed at a first lens barrel-proximal end portion that is a proximal end portion of the first lens barrel 40. An outer peripheral surface of the diameter-increased portion 40a is formed parallel to the longitudinal axis Ax.

The oblique-viewing optical system 52 (corresponding to a first optical system of the present invention) is composed of, for example, a plurality of lenses and a prism, and includes the light incident surface 52a that is inclined from a posture perpendicular to the longitudinal axis Ax and that faces the cover glass 39 and a light emitting surface 52b that has a posture perpendicular to the longitudinal axis Ax. The oblique-viewing optical system 52 refracts light, which is incident on the light incident surface 52a in a direction inclined with respect to the longitudinal axis Ax, in a direction parallel to the longitudinal axis Ax, and then guides the light to a lens system 58 provided in the second lens barrel 42 to be described later from the light emitting surface 52b. The configuration of the oblique-viewing optical system 52 is not particularly limited as long as light incident in a direction inclined with respect to the longitudinal axis Ax can be guided to the lens system 58.

A first lens barrel-proximal end surface 40b, which is a proximal end surface of the first lens barrel 40, that is, a proximal end surface of the diameter-increased portion 40a, is formed perpendicular to the longitudinal axis Ax. A fitting hole 40c is formed in the first lens barrel-proximal end surface 40b. An outer flange 42b of the second lens barrel 42 to be described later is fitted to the fitting hole 40c.

In a case where the already described rotary part 22b is rotated in the circumferential direction thereof, the first lens barrel 40 is rotated in the same direction as the rotary part 22b (the circumferential direction of the first lens barrel 40) via the sheath pipe 30, the protection sheath 32, and the cover 38.

FIG. 6 is a diagram illustrating the mounting of the cover 38 on the first lens barrel 40. As shown in FIG. 6, the first lens barrel 40 is provided with a pin-shaped positioning portion 54 that protrudes from a distal end side of the first lens barrel 40. The positioning portion 54 is engaged with a hole-shaped engaged portion 38a that is formed on an inner peripheral surface of the cover 38. Accordingly, the rotational position of the first lens barrel 40 in the cover 38 in the circumferential direction can be set to a position where the light incident surface 52a faces the cover glass 39. As a result, the mounting of the cover 38 on the first lens barrel 40 can be easily performed. The shapes and configurations of the positioning portion 54 and the engaged portion 38a can be appropriately changed.

Returning to FIGS. 2 to 5, the second lens barrel 42 is disposed on the proximal end side of the first lens barrel 40. The first lens barrel 40 and the second lens barrel 42 are rotatable relative to each other in the circumferential directions of the first lens barrel 40 and the second lens barrel 42 via the sliding part 44 and the pressing member 46 to be described later.

For example, the second lens barrel 42 is made of a metal material, such as stainless steel, and is formed substantially in the shape of a tube parallel to the longitudinal axis Ax. The second lens barrel 42 of this embodiment is formed to have a diameter smaller than the diameter of the diameter-increased portion 40a as a whole, but the shape of the second lens barrel 42 is not particularly limited as long as the diameter of at least a second lens barrel-distal end portion 42a, which is a distal end portion of the second lens barrel 42, is smaller than the diameter of the diameter-increased portion 40a. The lens system 58 corresponding to a second optical system of the present invention is housed in the second lens barrel 42.

The lens system 58 is composed of a plurality of lenses, and has the optical axis OA parallel to the longitudinal axis Ax. The lens system 58 guides light, which has passed through the oblique-viewing optical system 52, to the image pickup unit 50 to be described later.

An outer flange 42b corresponding to a first protruding portion of the present invention is provided around a distal end side of an outer peripheral surface of the second lens barrel-distal end portion 42a, that is, is formed in the circumferential direction of the outer peripheral surface. The outer flange 42b is formed to have an outer diameter corresponding to the diameter of the already described fitting hole 40c, and is fitted to the fitting hole 40c. Instead of the outer flange 42b, a plurality of engagement claws (not shown) may be provided around the outer peripheral surface of the second lens barrel-distal end portion 42a.

The sliding part 44 is made of, for example, ceramics and is formed substantially in the shape of a ring parallel to the longitudinal axis Ax. The sliding part 44 is formed separately from the second lens barrel 42, but is externally fitted and fixed to the outer peripheral surface of the second lens barrel-distal end portion 42a by a method such as adhesion, and is rotated integrally with the second lens barrel 42 in the circumferential direction thereof. The outer diameter of the sliding part 44 is the same (including substantially the same) as the outer diameter of the diameter-increased portion 40a. The sliding part 44 is in contact with the outer flange 42b from a proximal end side of the outer flange 42b, and is in contact with the diameter-increased portion 40a.

Further, the sliding part 44 includes a sliding part-distal end surface 44a that is a distal end surface of the sliding part 44 and a sliding part-proximal end surface 44b that is a proximal end surface of the sliding part 44 (see FIG. 5). The sliding part-distal end surface 44a and the sliding part-proximal end surface 44b are surfaces perpendicular to the longitudinal axis Ax. The sliding part-distal end surface 44a is in contact with the first lens barrel-proximal end surface 40b and the outer flange 42b. The sliding part-proximal end surface 44b is in contact with an inner flange 46b of the pressing member 46 to be described later.

For example, the pressing member 46 is made of a metal material, such as stainless steel, and is formed substantially in the shape of a tube parallel to the longitudinal axis Ax. The pressing member 46 is externally fitted over the sliding part 44 from the diameter-increased portion 40a. The pressing member 46 includes a pressing member-inner peripheral surface 46a and an inner flange 46b. Further, a proximal end portion of the pressing member 46 extends to the proximal end side beyond the proximal end portion of the already described sliding part 44.

The pressing member-inner peripheral surface 46a is in contact with both the outer peripheral surface of the diameter-increased portion 40a and an outer peripheral surface of the sliding part 44. The pressing member-inner peripheral surface 46a includes a fixed region R1 that is fixed to the outer peripheral surface of the diameter-increased portion 40a by a method such as adhesion, and a sliding region R2 with which the outer peripheral surface of the sliding part 44 is in sliding contact. Accordingly, the first lens barrel 40 and the pressing member 46 are fixed to each other not to be rotatable relative to each other in the circumferential direction thereof, but the sliding part 44 and the second lens barrel 42 are held to be rotatable relative to each other in the circumferential direction thereof. Therefore, the first lens barrel 40 and the second lens barrel 42 are rotatable relative to each other in the circumferential direction thereof via the sliding part 44 and the pressing member 46.

The inner flange 46b corresponds to a movement restricting portion and a second protruding portion of the present invention, and is provided around the pressing member-inner peripheral surface 46a at the proximal end portion of the pressing member 46. The inner flange 46b is in contact with the sliding part-proximal end surface 44b. A contact surface (distal end surface) of the inner flange 46b, which is in contact with the sliding part-proximal end surface 44b, is also a surface perpendicular to the longitudinal axis Ax. Accordingly, the inner flange 46b restricts the movement of the sliding part 44 in an axial direction of the longitudinal axis Ax (a direction along the longitudinal axis Ax, that is, a direction parallel to the longitudinal axis Ax) between the first lens barrel-proximal end surface 40b and the inner flange 46b. A plurality of engagement claws (not shown) provided around the pressing member-inner peripheral surface 46a may be used instead of the inner flange 46b.

In a case where the first lens barrel 40 and the second lens barrel 42 are rotated relative to each other in the circumferential directions thereof, as shown by a sliding surface SC of FIG. 4, the sliding part-distal end surface 44a and the first lens barrel-proximal end surface 40b slide on each other (sliding contact), the outer peripheral surface of the sliding part 44 and the sliding region R2 of the pressing member-inner peripheral surface 46a slide on each other, and the sliding part-proximal end surface 44b and the inner flange 46b slide on each other. In a case where the sliding part 44 is made of the same material (metal material) as at least one of the first lens barrel 40 and the pressing member 46 in this case, there is a concern that so-called galling (including adhesion, welding, or fusion welding) in which at least one of the first lens barrel 40 and the pressing member 46 is in close contact with the sliding part 44 will occur.

Accordingly, since the sliding part 44 is made of a material (ceramics in this embodiment) that is different from the materials of the first lens barrel 40 and the pressing member 46 and has good sliding between itself and the first lens barrel 40 and the pressing member 46 in this embodiment, the occurrence of the above-mentioned galling can be prevented.

As shown in FIGS. 2 and 3, for example, the holder 48 is made of a metal material, such as aluminum, and is formed substantially in the shape of a tube parallel to the longitudinal axis Ax. The holder 48 is connected and fixed (externally fitted and fixed) to a proximal end portion of the second lens barrel 42 from a proximal end side of the second lens barrel 42. Further, the holder 48 is fitted and fixed in a distal end-side opening portion of the already described connecting pipe 34. Accordingly, the second lens barrel 42, the holder 48, and the connecting pipe 34 are integrally rotated in the circumferential direction.

The image pickup unit 50 to be described later is held, more specifically, a prism 50a of the image pickup unit 50 is held at a proximal end-side opening portion of the holder 48. Accordingly, the image pickup unit 50 is rotated integrally with the second lens barrel 42 in the circumferential direction via the holder 48.

The image pickup unit 50 picks up the image of light that is incident through the oblique-viewing optical system 52 and the lens system 58. The image pickup unit 50 comprises a prism 50a, an image pickup element 50b, and a circuit board 50c.

The prism 50a corresponds to a refractive optical element of the present invention, and is held at the proximal end-side opening portion of the holder 48 as already described. The prism 50a refracts light, which is incident through the lens system 58, by 90°.

Since the image pickup element 50b is fixed to the prism 50a in a state where the image pickup element 50b is mounted on the circuit board 50c, the image pickup element 50b picks up the image of the light refracted by the prism 50a. A charge coupled device (CCD) image sensor or a complementary metal oxide semiconductor (CMOS) image sensor can be used as the image pickup element 50b.

The circuit board 50c controls the drive of the image pickup element 50b. Further, the distal end portion of the signal cable 26 is connected to the circuit board 50c via a connector 60. Furthermore, the circuit board 50c outputs image pickup signals of the image pickup element 50b to the signal cable 26 via the connector 60.

Figure 7:
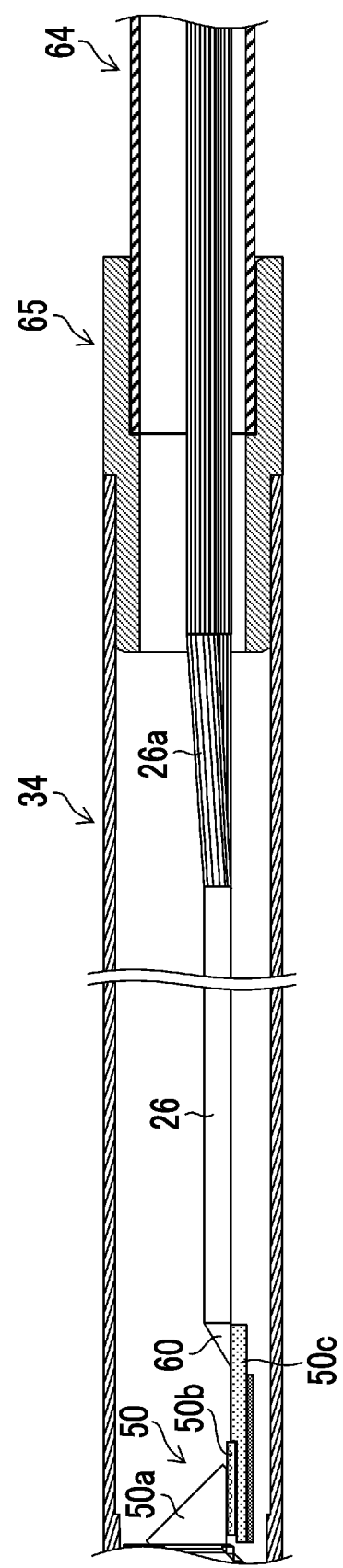
FIG. 7 is a cross-sectional view of a connecting pipe.

FIG. 7 is a cross-sectional view of the connecting pipe 34. As shown in FIG. 7, a cable proximal end portion opposite to the cable distal end portion of the signal cable 26 to be connected to the circuit board 50c (image pickup unit 50) has a torsionally deformable loose wire structure 26a, that is, a structure in which a plurality of signal lines of the signal cable 26 are separated from each other without being integrated. Accordingly, in a case where the second lens barrel 42 is rotated relative to the first lens barrel 40 in the circumferential direction thereof, that is, in a case where the image pickup unit 50 is rotated in the circumferential direction, the disconnection of the signal cable 26 is prevented.

A distal end portion of the torque tube 64 is fitted and connected to a proximal end-side opening portion of the connecting pipe 34 via a connecting member 65. The connecting pipe 34 and the torque tube 64 may be directly connected to each other without the connecting member 65. Further, a proximal end portion of the torque tube 64 is connected to the cable holding part 23a as already described.

The torque tube 64 is a tubular coil body in which a plurality of strands (not shown) are wound in a helical shape along the longitudinal axis Ax. The torque tube 64 transmits the rotary torque of the base 22a of the operation unit 22 (cable holding part 23a) to the second lens barrel 42 via the connecting pipe 34 and the like. Since the torque tube 64 is used in this case, the transmission of torque other than rotary torque to the connecting pipe 34 and the like is suppressed. Accordingly, durability of the connecting pipe 34 and the like can be improved. A coil body (a coil spring or the like) in which a single strand is wound in a helical shape along the longitudinal axis Ax may be used as the torque tube 64.

The rotary torque mentioned here also includes torque (posture maintenance torque) that maintains the posture of the second lens barrel 42 relative to the first lens barrel 40 in the circumferential direction in addition to torque that rotates the second lens barrel 42 relative to the first lens barrel 40 in the circumferential direction. Accordingly, even in a case where the rotary part 22b is operated to rotate so that the first lens barrel 40 is rotated in the circumferential direction thereof, the posture of the second lens barrel 42 in the circumferential direction can be maintained.

Figure 8:
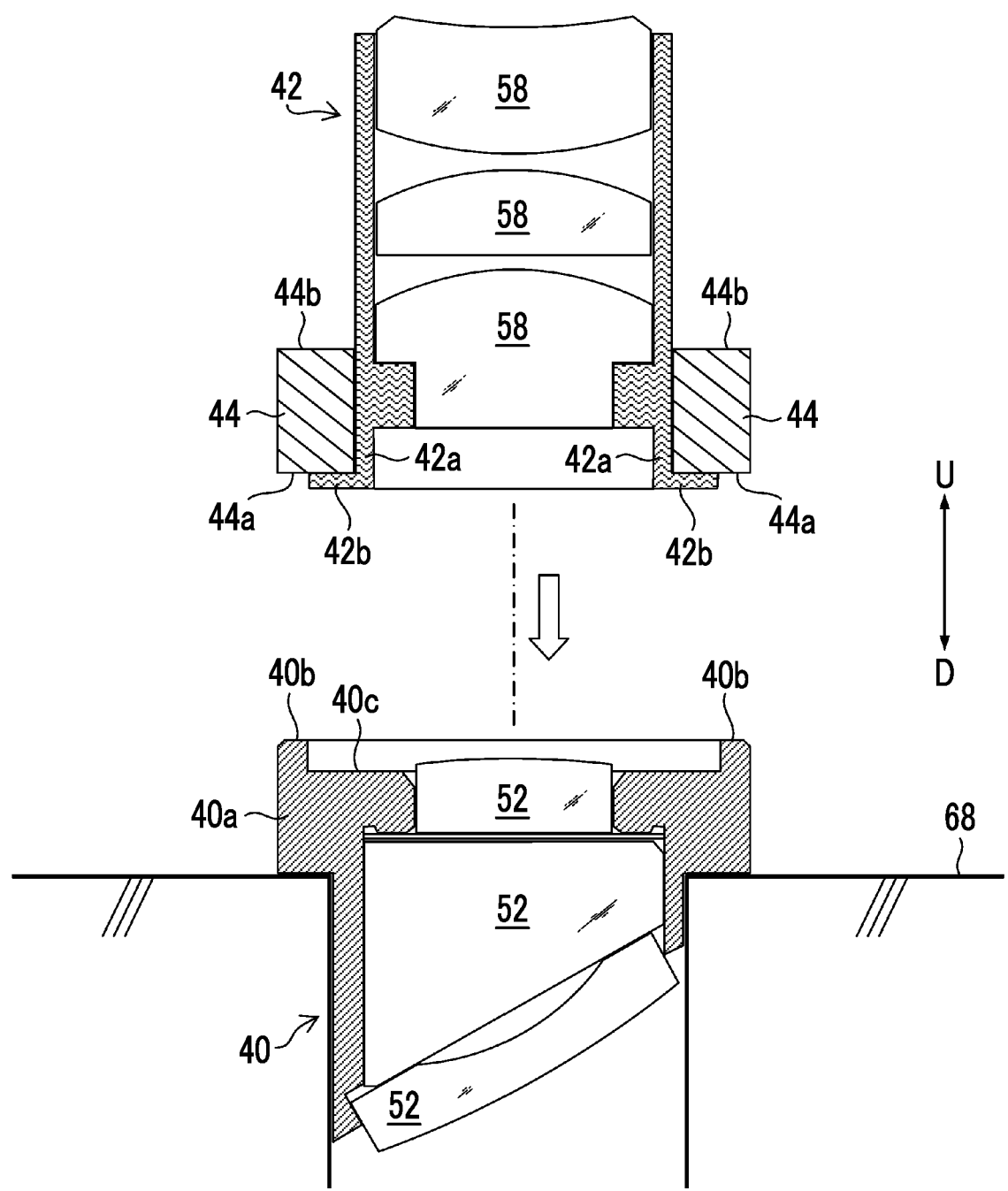
FIG. 8 is a diagram illustrating the assembly of the image pickup device according to the first embodiment, particularly, the assembly of the first lens barrel, the second lens barrel, the sliding part, and the pressing member.
Figure 9:
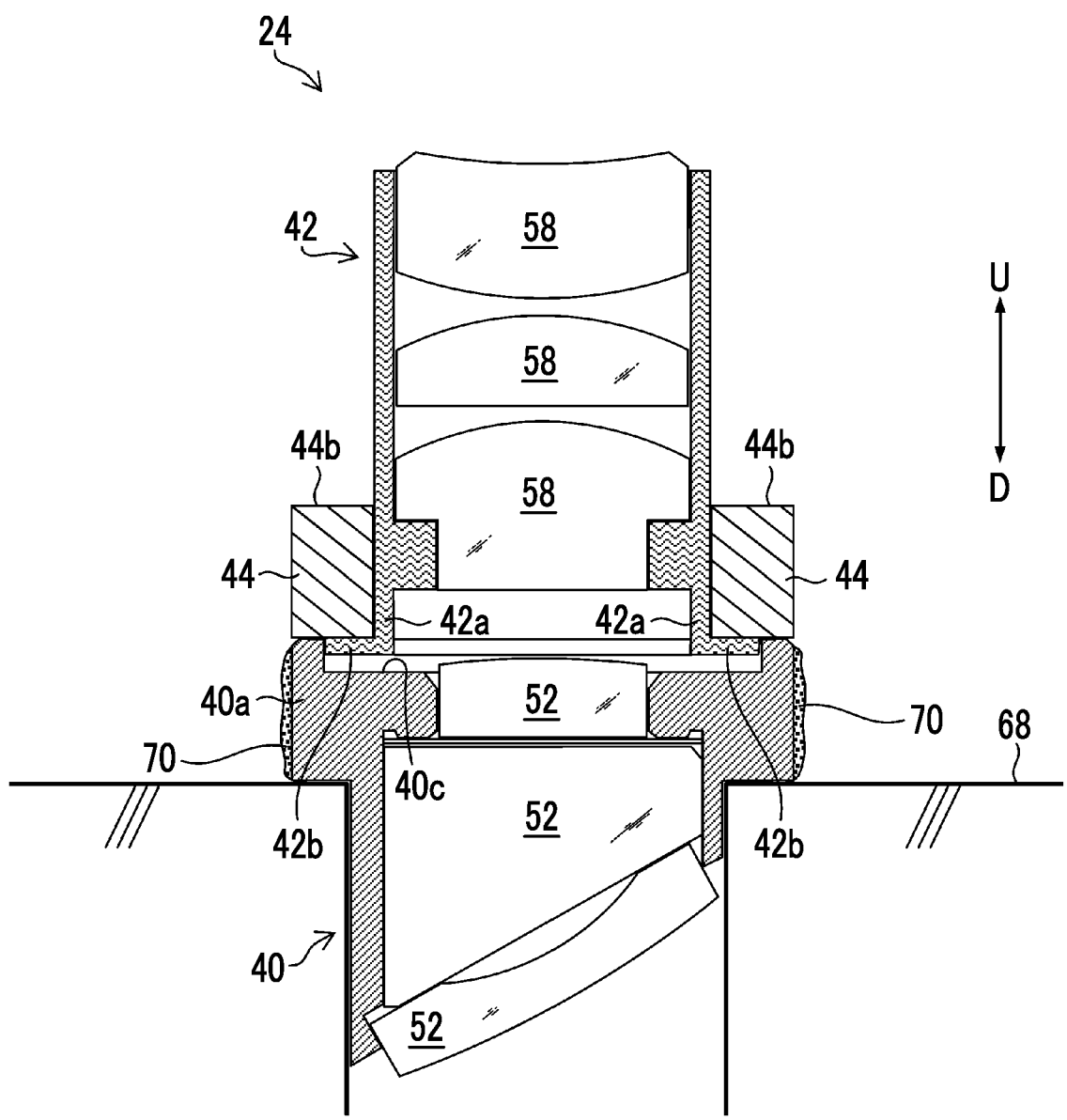
FIG. 9 is a diagram illustrating the assembly of the image pickup device according to the first embodiment, particularly, the assembly of the first lens barrel, the second lens barrel, the sliding part, and the pressing member.
Figure 10:
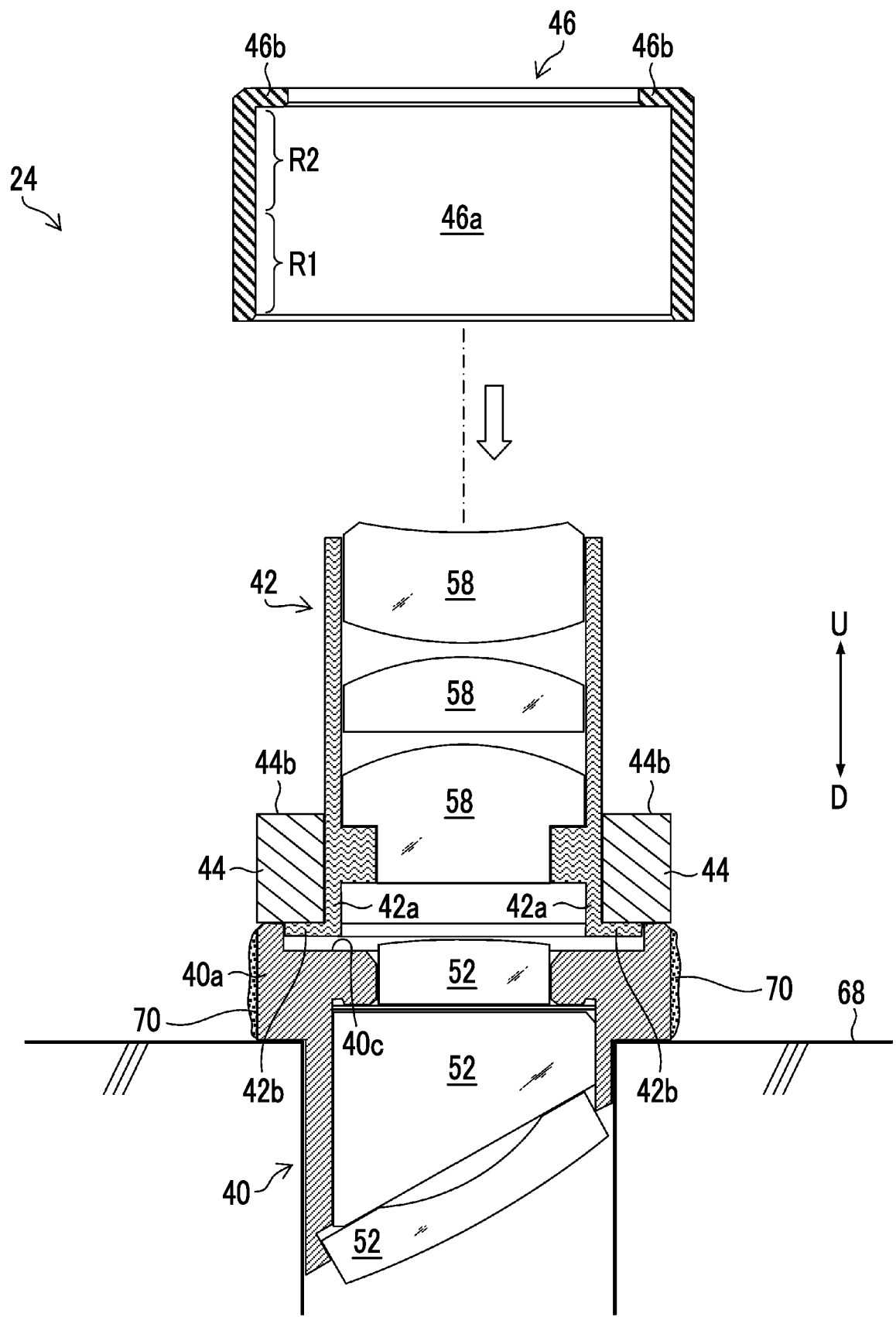
FIG. 10 is a diagram illustrating the assembly of the image pickup device according to the first embodiment, particularly, the assembly of the first lens barrel, the second lens barrel, the sliding part, and the pressing member.

FIGS. 8 to 10 are diagrams illustrating the assembly of the image pickup device 24 according to the first embodiment, particularly, the assembly of the first lens barrel 40, the second lens barrel 42, the sliding part 44, and the pressing member 46. In each drawing, reference character U indicates an upward direction (vertically upward), and reference character D indicates a downward direction (vertically downward). Further, the positioning portion 54 of the first lens barrel 40 is appropriately omitted in FIGS. 8 to 10 in order to not complicate the drawings.

First, the first lens barrel 40 is set on a support table 68 in a state where the distal end side of the first lens barrel 40 faces downward as shown in FIG. 8. Then, the outer flange 42b of the second lens barrel 42 to which the sliding part 44 is externally fitted and fixed in advance is fitted to the fitting hole 40c of the first lens barrel 40. Accordingly, the sliding part-distal end surface 44a of the sliding part 44 is abutted against the first lens barrel-proximal end surface 40b of the first lens barrel 40 using the outer flange 42b and the fitting hole 40c as guides.

Then, an adhesive 70 is applied to the outer peripheral surface of the diameter-increased portion 40a as shown in FIG. 9. After the adhesive 70 is applied, the pressing member 46 is fitted to the outer peripheral surfaces of both the diameter-increased portion 40a and the sliding part 44 from the proximal end side of the second lens barrel 42 as shown in FIG. 10, and the inner flange 46b is abutted against the sliding part-proximal end surface 44b. Accordingly, the pressing member 46 is externally fitted over the outer peripheral surfaces of both the diameter-increased portion 40a and the sliding part 44, and the pressing member 46 adheres and is fixed to the outer peripheral surface of the diameter-increased portion 40a. In this case, it is preferable that a weight (not shown) is mounted on a proximal end side (a side corresponding to the upward direction U) of the inner flange 46*b* to reliably abut the sliding part-distal end surface 44*a* against the first lens barrel-proximal end surface 40*b* and to reliably abut the inner flange 46*b* against the sliding part-proximal end surface 44*b*.

After the pressing member 46 adheres and is fixed, the holder 48 is externally fitted and fixed to the second lens barrel 42, and the prism 50*a* of the image pickup unit 50 is fixed to the proximal end-side opening portion of the holder 48. The assembly of the image pickup device 24 is completed as described above.

Since the sliding part-distal end surface 44*a* is abutted against the first lens barrel-proximal end surface 40*b* and the inner flange 46*b* is abutted against the sliding part-proximal end surface 44*b* in the first embodiment as described above, parallelism between the first lens barrel 40 and the second lens barrel 42 can be ensured, and backlash can be prevented. Accordingly, the surface tilt (the tilt of the optical axis OA) of the oblique-viewing optical system 52 of the first lens barrel 40 and the lens system 58 of the second lens barrel 42 can be prevented. That is, since the component accuracy of the first lens barrel 40, the second lens barrel 42, the sliding part 44, and the pressing member 46 (the surface accuracy of the sliding surface SC) is ensured in the first embodiment, it is possible to prevent the above-mentioned surface tilt without requiring complicated optical adjustment during the assembly of the image pickup device 24.

Further, since the outer flange 42*b* is fitted to the fitting hole 40*c* and the pressing member-inner peripheral surface 46*a* is in contact with the outer peripheral surfaces of both the diameter-increased portion 40*a* and the sliding part 44 in the first embodiment, the first lens barrel 40 and the second lens barrel 42 can be automatically aligned. That is, since the component accuracy of the first lens barrel 40, the second lens barrel 42, the sliding part 44, and the pressing member 46 is ensured in the first embodiment, it is possible to prevent the deflection of the optical axes (the eccentricity of the optical axis OA) of the oblique-viewing optical system 52 and the lens system 58 without requiring complicated optical adjustment during the assembly of the image pickup device 24. Furthermore, since the automatic alignment of the first lens barrel 40 and the second lens barrel 42 described above can be realized with a small number of components, it is possible to reduce the accumulation of tolerances of the respective components.

As described above, in the first embodiment, the occurrence of a surface tilt, the deflection of the optical axes, and backlash is suppressed without requiring complicated optical adjustment during the assembly of the image pickup device 24, so that good optical performance of the image pickup device 24 is obtained. Further, since complicated optical adjustment is not required, it is possible to reduce the occurrence of defective products that fail image quality inspection after the assembly and adjustment of the image pickup device 24 (oblique-viewing endoscope 10).

Second Embodiment

Figure 11:
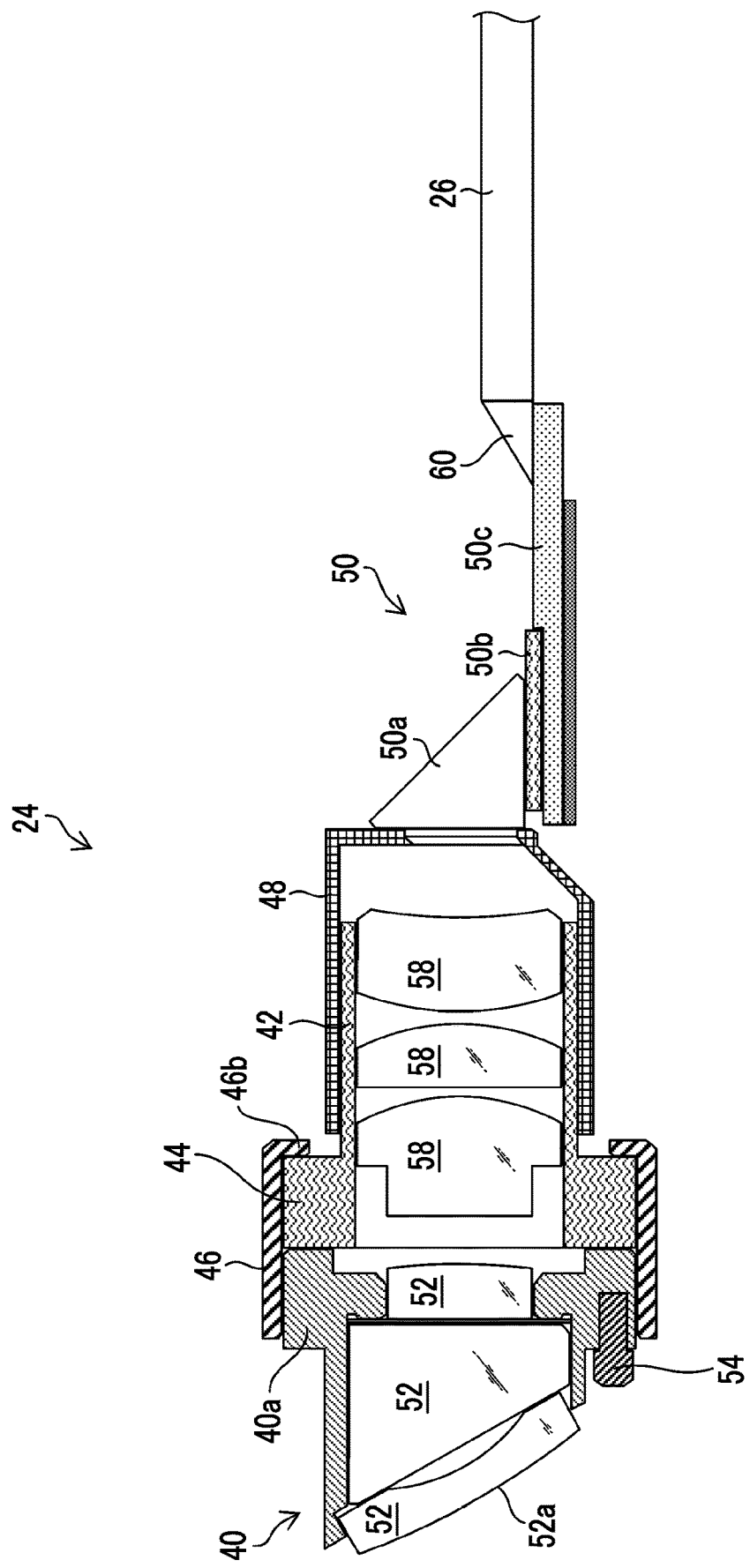
FIG. 11 is a cross-sectional view of an image pickup device according to a second embodiment.

FIG. 11 is a cross-sectional view of an image pickup device 24 according to a second embodiment. The second lens barrel 42 and the sliding part 44 are formed separately from each other in the image pickup device 24 according to the first embodiment, but the image pickup device 24 according to the second embodiment comprises an integrally molded body in which a second lens barrel 42 and a sliding part 44 are formed integrally with each other. Since the image pickup device 24 and an oblique-viewing endoscope 10 of the second embodiment have basically the same configuration as in the first embodiment except that the integrally molded body in which the second lens barrel 42 and the sliding part 44 are formed integrally with each other is provided, parts having the same functions or configurations as in the first embodiment will be denoted by the same reference numerals as those of the first embodiment, and the description thereof will be omitted.

As shown in FIG. 11, the sliding part 44 is integrally formed on an outer peripheral surface of a second lens barrel-distal end portion 42*a*, and the formation of an outer flange 42*b* is omitted in the second lens barrel 42 of the second embodiment. In this case, as in the first embodiment, since a sliding part-distal end surface 44*a* is abutted against a first lens barrel-proximal end surface 40*b* and an inner flange 46*b* is abutted against a sliding part-proximal end surface 44*b*, a surface tilt and backlash can be prevented. Further, since a pressing member-inner peripheral surface 46*a* is in contact with the outer peripheral surfaces of both a diameter-increased portion 40*a* and the sliding part 44, the deflection of optical axes can be prevented. As a result, the same effects as those of the first embodiment are obtained.

Furthermore, since the second lens barrel 42 and the sliding part 44 are formed integrally with each other in the second embodiment, it is not necessary to externally fit and fix the sliding part 44 to the outer peripheral surface of the second lens barrel-distal end portion 42*a*. Accordingly, assembly man-hours can be reduced.

In a case where the sliding part 44 is made of the same material (metal material) as at least one of a first lens barrel 40 and a pressing member 46, there is a concern that the above-mentioned galling will occur. For this reason, in the second embodiment, the first lens barrel 40 and the pressing member 46 are made of, for example, stainless steel as in the first embodiment, and the second lens barrel 42 and the sliding part 44 are made of, for example, brass. Accordingly, the occurrence of the above-mentioned galling can also be prevented in the second embodiment. As long as the material of the sliding part 44 (second lens barrel 42) and the material of the first lens barrel 40 and of the pressing member 46 are different from each other, these materials are not particularly limited.

Figure 12:
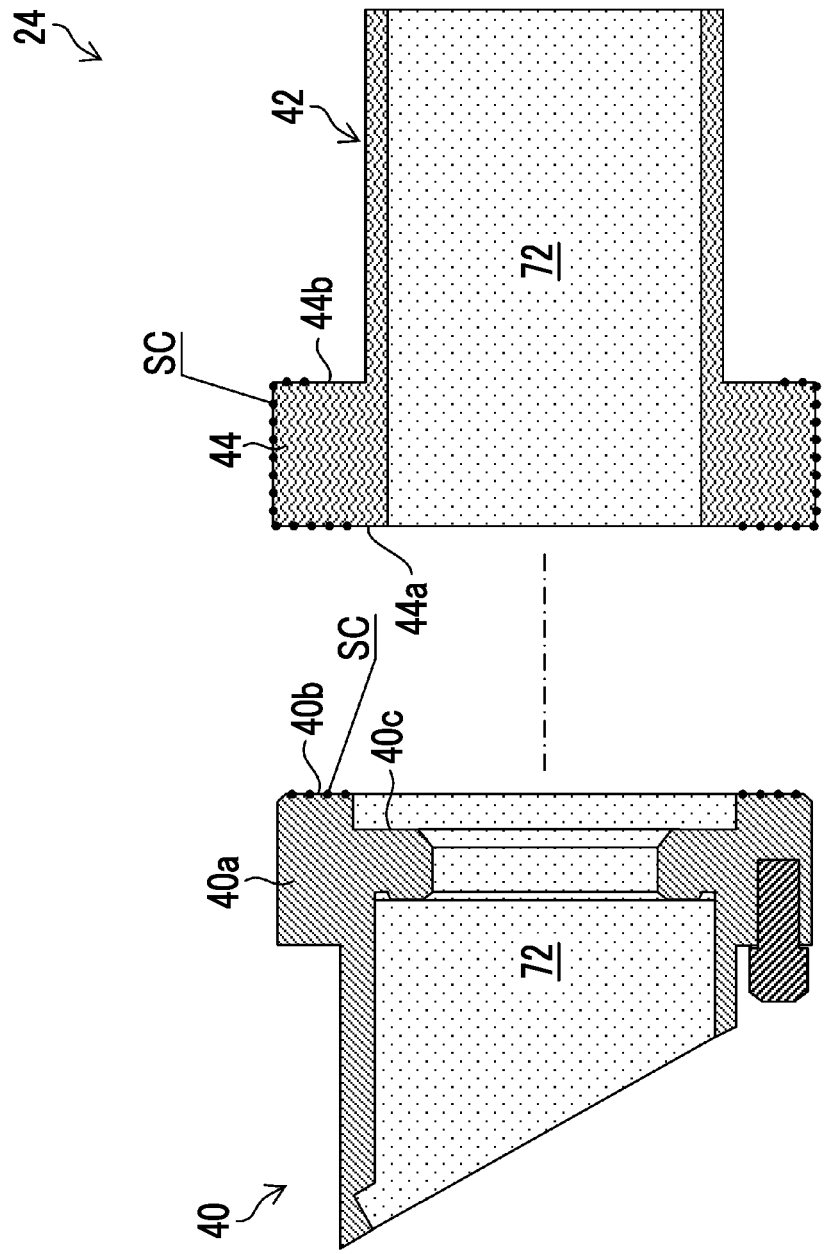
FIG. 12 is a diagram illustrating a black layer that is formed on inner peripheral surfaces of a first lens barrel and a second lens barrel.

FIG. 12 is a diagram illustrating a black layer 72 that is formed on the inner peripheral surfaces of the first lens barrel 40 and the second lens barrel 42. As shown in FIG. 12, the black layer 72 (also referred to as a black film) corresponding to an antireflection layer of the present invention is formed on the inner peripheral surfaces of both the first lens barrel 40 and the second lens barrel 42 by a publicly known black treatment, such as application or plating. The black layer 72 corresponds to the antireflection layer of the present invention, and absorbs light to prevent the reflection of light on the inner peripheral surfaces of both the first lens barrel 40 and the second lens barrel 42.

In this case, high dimensional accuracy is required for a sliding surface SC between the first lens barrel 40 and the sliding part 44 and a sliding surface SC between the sliding part 44 and the pressing member 46. For this reason, in order to eliminate the influence of the thickness of the black layer 72, which is formed by the black treatment, on tolerance, the above-mentioned sliding surfaces SC, that is, the first lens barrel-proximal end surface 40*b*, the sliding part-distal end surface 44*a*, the outer peripheral surface of the sliding part 44, and the sliding part-proximal end surface 44*b*, are formed as surfaces on which the black layer 72 is not formed. Accordingly, the reflection of light in the first lens barrel 40 and the second lens barrel 42 is suppressed, and the high dimensional accuracy of the sliding surfaces SC can be ensured.

In the image pickup device 24 according to the first embodiment, the black layer 72 may also be likewise formed on the inner peripheral surfaces of both the first lens barrel 40 and the second lens barrel 42.

[Other]

Figure 13:
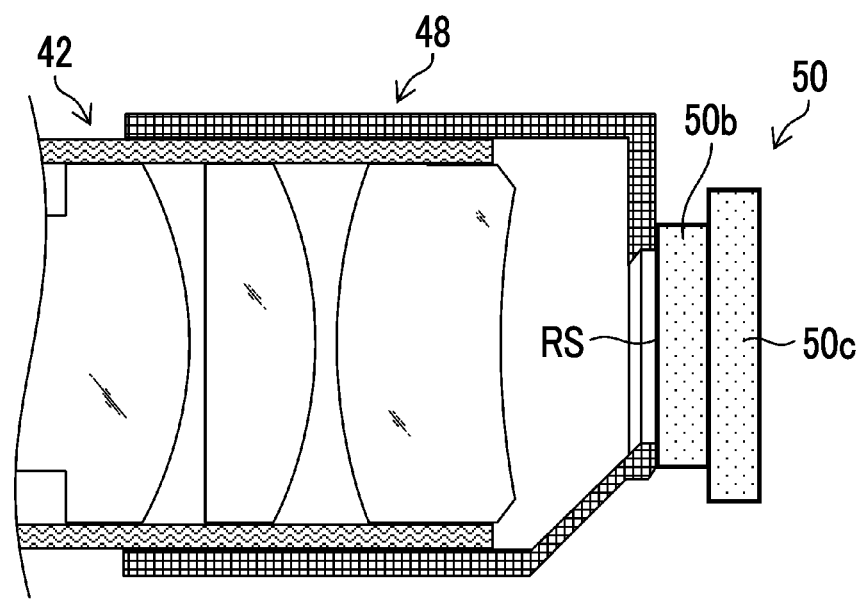
FIG. 13 is a diagram illustrating a modification example of an image pickup unit.

FIG. 13 is a diagram illustrating a modification example of the image pickup unit 50. The image pickup unit 50 of each of the above-mentioned embodiments refracts light, which is incident through the oblique-viewing optical system 52 and the lens system 58, via the prism 50a and then picks up an image via the image pickup element 50b. However, the image pickup unit 50 may pick up an image via the image pickup element 50b without refracting this light via the prism 50a. In this case, an image pickup element 50b is held at a proximal end-side opening portion of a holder 48 as shown in FIG. 13. This image pickup element 50b is held by the holder 48 at a posture perpendicular to the longitudinal axis Ax (the optical axis OA of the lens system 58), and includes a light-receiving surface RS orthogonal to the optical axis OA of the lens system 58.

In each of the above-mentioned embodiments, the pressing member 46 is fixed to the outer peripheral surface of the diameter-increased portion 40a and is slidable on the outer peripheral surface of the sliding part 44. However, the pressing member 46 may be fixed to the outer peripheral surface of the sliding part 44 and may be slidable on the outer peripheral surface of the diameter-increased portion 40a. In this case, an inner flange 46b is provided around the pressing member-inner peripheral surface 46a at a distal end portion of the pressing member 46. Further, in a case where inner flanges 46b are provided around the pressing member-inner peripheral surface 46a at both the distal end portion and a proximal end portion of the pressing member 46, the pressing member 46 may be slidable on both the outer peripheral surface of the diameter-increased portion 40a and the outer peripheral surface of the sliding part 44.

The diameter-increased portion 40a is formed on the first lens barrel 40 in each of the above-mentioned embodiments, but the entire first lens barrel 40 may be formed to have the same outer diameter as the diameter-increased portion 40a. In this case, the pressing member 46 may be externally fitted to the entire region of the outer peripheral surface of the first lens barrel 40.

The outer diameter of the second lens barrel-distal end portion 42a of the second lens barrel 42 and the outer diameter of the proximal end portion of the second lens barrel 42 are equal to each other in each of the above-mentioned embodiments, but the outer diameters of both the distal end portion and the proximal end portion of the second lens barrel 42 may not be equal to each other.

The outer diameter of the diameter-increased portion 40a and the outer diameter of the sliding part 44 are equal to each other in each of the above-mentioned embodiments, but the outer diameters of both the diameter-increased portion 40a and the sliding part 44 may not be equal to each other as long as the pressing member 46 can be externally fitted.

The second lens barrel 42 and the holder 48 are formed separately from each other in each of the above-mentioned embodiments, but both the second lens barrel 42 and the holder 48 may be molded integrally with each other.

The image pickup device 24 is provided with the holder 48 and the image pickup unit 50 in each of the above-mentioned embodiments, but the first lens barrel 40, the second lens barrel 42, the sliding part 44, and the pressing member 46 of the image pickup device 24 according to the embodiment of the present invention may be dealt as one unit.

A rigid endoscope has been described as the oblique-viewing endoscope 10 by way of example in each of the above-mentioned embodiments, but the present invention can also be applied to the case of a flexible endoscope. Further, the oblique-viewing endoscope 10 has been described as an endoscope of the present invention by way of example in each of the above-mentioned embodiments, but the present invention can be applied to various endoscopes including the first lens barrel 40 and the second lens barrel 42 and image pickup devices thereof.

EXPLANATION OF REFERENCES

10: oblique-viewing endoscope
12: endoscope system
14: processor device
16: monitor
18: light source device
20: insertion unit
22: operation unit
22a: base
22b: rotary part
22c: air-tight case
23a: cable holding part
23b: partition wall
24: image pickup device
26: signal cable
26a: loose wire structure
27: signal cable
28: light guide
30: sheath pipe
31: insertion passage
32: protection sheath
34: connecting pipe
36: cover holding part
38: cover
38a: engaged portion
39: cover glass
40: first lens barrel
40a: diameter-increased portion
40b: first lens barrel-proximal end surface
40c: fitting hole
42: second lens barrel
42a: second lens barrel-distal end portion
42b: outer flange
44: sliding part
44a: sliding part-distal end surface
44b: sliding part-proximal end surface
46: pressing member
46a: pressing member-inner peripheral surface
46b: inner flange
48: holder
50: image pickup unit
50a: prism
50b: image pickup element
50c: circuit board
52: oblique-viewing optical system
52a: light incident surface
52b: light emitting surface
54: positioning portion
58: lens system
60: connector
64: torque tube
65: connecting member 68: support table
70: adhesive
72: black layer
Ax: longitudinal axis
OA: optical axis
R1: fixed region
R2: sliding region
RS: light-receiving surface
SC: sliding surface

What is claimed is:

1. An image pickup device that is provided at a distal end portion of an insertion unit of an endoscope having a longitudinal axis, the image pickup device comprising:
   a first lens barrel that houses a first optical system;
   a second lens barrel that is disposed on a proximal end side of the first lens barrel, houses a second optical system on which light having passed through the first optical system is to be incident, and includes a second lens barrel-distal end portion that is a distal end portion having a diameter smaller than a diameter of a first lens barrel-proximal end portion which is a proximal end portion of the first lens barrel;
   a sliding part that is provided around an outer peripheral surface of the second lens barrel-distal end portion and that is in contact with a first lens barrel-proximal end surface which is a proximal end surface of the first lens barrel-proximal end portion; and
   a pressing member that is externally fitted over the sliding part from the first lens barrel-proximal end portion,
   wherein the pressing member includes:
      a pressing member-inner peripheral surface that is in contact with both an outer peripheral surface of the first lens barrel-proximal end portion and an outer peripheral surface of the sliding part; and
      a movement restricting portion that restricts a relative movement of the sliding part in an axial direction of the longitudinal axis with respect to the first lens barrel, the movement restricting portion being in contact with a sliding part-proximal end surface which is a proximal end surface of the sliding part, and
   the first lens barrel and the second lens barrel are rotatable relative to each other in circumferential directions of the first lens barrel and the second lens barrel via the sliding part and the pressing member.

2. The image pickup device according to claim 1, further comprising:
   an image pickup unit that picks up an image of light incident through the first optical system and the second optical system.

3. The image pickup device according to claim 2,
   wherein the image pickup unit includes a refractive optical element that refracts light incident from the second optical system, and an image pickup element that picks up an image of the light refracted by the refractive optical element.

4. The image pickup device according to claim 2,
   wherein the image pickup unit includes an image pickup element that is disposed on a proximal end side of the second optical system and that includes a light-receiving surface orthogonal to an optical axis of the second optical system.

5. The image pickup device according to claim 3, further comprising:
   a tubular holder that is connected and fixed to the second lens barrel from a proximal end side of the second lens barrel and that holds the image pickup unit.

6. The image pickup device according to claim 1,
   wherein the second lens barrel and the sliding part are formed separately from each other, and the sliding part is externally fitted and fixed to the outer peripheral surface of the second lens barrel-distal end portion.

7. The image pickup device according to claim 6, further comprising:
   a first protruding portion that is provided around a distal end side of the outer peripheral surface of the second lens barrel-distal end portion; and
   a fitting hole which is formed in a first lens barrel-proximal end surface that is a proximal end surface of the first lens barrel-proximal end portion and to which the first protruding portion is fitted,
   wherein the sliding part is externally fitted and fixed to the outer peripheral surface of the second lens barrel-distal end portion in a state where the sliding part is in contact with the first protruding portion from a proximal end side of the first protruding portion.

8. The image pickup device according to claim 1, further comprising:
   an integrally molded body in which the second lens barrel-distal end portion of the second lens barrel and the sliding part are integrated with each other.

9. The image pickup device according to claim 1,
   wherein a material of the sliding part is different from a material of the first lens barrel and a material of the pressing member.

10. The image pickup device according to claim 1,
    wherein the pressing member-inner peripheral surface includes a fixed region that is fixed to the outer peripheral surface of the first lens barrel-proximal end portion, and a sliding region with which the outer peripheral surface of the sliding part is in sliding contact.

11. The image pickup device according to claim 1, further comprising:
    an antireflection layer that is formed on an inner peripheral surface of the first lens barrel and on an inner peripheral surface of the second lens barrel,
    wherein a surface of the first lens barrel that is in contact with the sliding part and surfaces of the sliding part that are in contact with the first lens barrel and the pressing member are surfaces on which the antireflection layer is not formed.

12. The image pickup device according to claim 1,
    wherein the first lens barrel-proximal end portion is a diameter-increased portion of which a diameter is larger than diameters of other portions of the first lens barrel.

13. The image pickup device according to claim 1,
    wherein an outer diameter of the first lens barrel-proximal end portion and an outer diameter of the sliding part are equal to each other.

14. The image pickup device according to claim 1,
    wherein the first lens barrel-proximal end surface and a sliding part-distal end surface that is a distal end surface of the sliding part are surfaces perpendicular to the longitudinal axis,
    the sliding part-distal end surface is in contact with the first lens barrel-proximal end surface, and
    the movement restricting portion restricts the movement of the sliding part in the axial direction between the first lens barrel-proximal end surface and the movement restricting portion.

15. The image pickup device according to claim 14,
wherein a proximal end portion of the pressing member extends to a proximal end side beyond a proximal end portion of the sliding part,
the movement restricting portion is a second protruding portion that is provided around the pressing member-inner peripheral surface at the proximal end portion of the pressing member,
the second protruding portion is in contact with the sliding part-proximal end surface restrict the movement of the sliding part in the axial direction between the first lens barrel-proximal end surface and the second protruding portion, and
the sliding part-proximal end surface and a contact surface of the second protruding portion, which is in contact with the sliding part-proximal end surface, are surfaces perpendicular to the longitudinal axis.

16. The image pickup device according to claim 1,
wherein the first optical system is an oblique-viewing optical system that guides light, which is incident in a direction inclined with respect to the longitudinal axis, to the second optical system.

17. The image pickup device according to claim 16,
wherein the oblique-viewing optical system includes a light incident surface that is inclined from a posture perpendicular to the longitudinal axis, and includes
   a tubular cover that is provided at a distal end portion of the first lens barrel and that covers the distal end portion of the first lens barrel,
   a cover glass that is provided at a distal end portion in the cover and that has an inclined posture corresponding to an inclination angle of the light incident surface, and
   a positioning portion that is provided on the first lens barrel and that is engaged with an engaged portion provided in the cover to set a rotational position of the first lens barrel in the cover in the circumferential direction to a position where the light incident surface faces the cover glass.

18. The image pickup device according to claim 1, further comprising:
   an image pickup unit that picks up an image of light incident through the first optical system and the second optical system; and
   a cable that is connected to the image pickup unit,
wherein a cable proximal end portion opposite to a cable distal end portion of the cable to be connected to the image pickup unit is adapted to be torsionally deformable.

19. An endoscope comprising:
an insertion unit that has a longitudinal axis; and
the image pickup device according to claim 1 that is provided at a distal end portion of the insertion unit.

20. The endoscope according to claim 19,
wherein the image pickup device includes
   an image pickup unit that picks up an image of light incident through the first optical system and the second optical system, and
   a tubular holder that is connected and fixed to the second lens barrel from a proximal end side of the second lens barrel and that holds the image pickup unit, and
the endoscope includes
   a tubular torque tube that is rotatable in the circumferential direction, and
   a tubular connecting pipe that connects the holder to the torque tube and that transmits rotary torque of the torque tube to the holder.

\* \* \* \* \*